(12) United States Patent
Huang et al.

(10) Patent No.: US 10,488,322 B2
(45) Date of Patent: Nov. 26, 2019

(54) SYSTEM AND METHOD FOR CAPTURING AND RETRIEVING BIOLOGICAL PARTICLES AND CAPTURING DEVICE USED IN THE SAME

(71) Applicant: CE Biotechnology, Inc., Apia (WS)

(72) Inventors: Chung-Er Huang, Apia (WS); Sheng-Wen Chen, Apia (WS); Hsin-Cheng Ho, Apia (WS); Ming Chen, Apia (WS)

(73) Assignee: CE BIOTECHNOLOGY, INC., Apia (WS)

( * ) Notice: Subject to any disclaimer, the term of this patent is extended or adjusted under 35 U.S.C. 154(b) by 303 days.

(21) Appl. No.: 15/469,111

(22) Filed: Mar. 24, 2017

(65) Prior Publication Data
US 2017/0299495 A1    Oct. 19, 2017

(30) Foreign Application Priority Data
Apr. 14, 2016 (TW) .............................. 105111590 A

(51) Int. Cl.
G01N 15/14    (2006.01)
B01L 3/00    (2006.01)
G01N 15/10    (2006.01)

(52) U.S. Cl.
CPC .... *G01N 15/1484* (2013.01); *B01L 3/502761* (2013.01); *B01L 2200/0668* (2013.01);
(Continued)

(58) Field of Classification Search
CPC ......... B01L 3/502753; B01L 3/502761; B01L 3/5027; B01L 3/502707; B01L 3/50273;
(Continued)

(56) References Cited

U.S. PATENT DOCUMENTS

2011/0139620 A1 *  6/2011  Stumber ................. B01F 5/061
                                                    204/451
2011/0247938 A1    10/2011  Wang et al.
(Continued)

FOREIGN PATENT DOCUMENTS

CN        1882838 A    12/2006
CN        1920559 A    2/2007
(Continued)

OTHER PUBLICATIONS

Search Report and Office Action, issued to Chinese counterpart application No. 201610839160.4 by the CNIPA dated Jan. 25, 2019, with an English translation thereof.

*Primary Examiner* — David C Mellon
(74) *Attorney, Agent, or Firm* — Ladas & Parry, LLP

(57) ABSTRACT

A biological particle capturing and retrieving system includes a capturing device including a substrate, an isolating layer and a driving unit, and a retrieving device including a micropipette. The isolating layer includes a top surface, multiple pores, and multiple fluidic grooves indented from the top surface, arranged in a herringbone pattern, and each having a bottom surface. The pores are formed in the bottom surfaces of the fluidic grooves, and each capture a biological particle in a liquid sample. The driving unit drives the liquid sample to flow by electrowetting through the pores. The micropipette has a carrier coated with a biological particle-binding material binding with the biological particle received in a corresponding pore.

9 Claims, 6 Drawing Sheets

(52) U.S. Cl.
CPC .......... *B01L 2300/0636* (2013.01); *B01L 2300/0816* (2013.01); *B01L 2300/0825* (2013.01); *B01L 2400/0427* (2013.01); *G01N 2015/1006* (2013.01)

(58) Field of Classification Search
CPC ...... B01L 3/021; B01L 3/0217; B01L 3/0227; B01L 3/0234; B01L 3/0237; B01L 2400/0427; B01L 2300/0825; B01L 2300/0816; B01L 2300/0636; B01L 2200/0668; B01L 2300/0819; B01L 2300/0829; B01L 3/5085; B01L 3/5088; B81B 1/00; B81B 1/002; B81B 1/006; B81B 1/008; G01N 15/1056; G01N 15/10; G01N 15/1484; G01N 2015/1006; B03C 1/28; B03C 1/286; B03C 1/288; B03C 1/30

See application file for complete search history.

(56) References Cited

U.S. PATENT DOCUMENTS

| | | | | |
|---|---|---|---|---|
| 2012/0129716 A1* | 5/2012 | Chee | ................. | B01L 3/502761 506/9 |
| 2015/0226741 A1* | 8/2015 | Liu | ..................... | G01N 33/574 435/7.24 |
| 2019/0001320 A1* | 1/2019 | Huang | ............... | G01N 33/5438 |

FOREIGN PATENT DOCUMENTS

| | | | |
|---|---|---|---|
| CN | 102296028 A | 12/2011 | |
| CN | 103894248 A | 7/2014 | |
| WO | 2011035177 A2 | 3/2011 | |

* cited by examiner

SYSTEM AND METHOD FOR CAPTURING AND RETRIEVING BIOLOGICAL PARTICLES AND CAPTURING DEVICE USED IN THE SAME

CROSS-REFERENCE TO RELATED APPLICATION

This application claims priority to Taiwanese Patent Application No. 105111590, filed on Apr. 14, 2016 the disclosure of which is incorporated herein by reference.

FIELD

The disclosure relates to a device, system and a method for capturing and retrieving biological particles, and more particularly to a system, a method, and a capturing device that can capture and retrieve a single target biological particle.

BACKGROUND

Cancer is one of the leading causes of death among humans. Although the mechanism for cancer development is not yet fully understood, it is believed that the metastasis of cancer cells contributes to the cause of death by cancer. In this case, the cancer cells proliferate, and spread to other parts of human body though the lymphatic system or vascular system. Such cancer cells are called circulating tumor cells (CTCs).

The detection of the circulating tumor cells has become one of the main topics in the field of cancer research. There are many different techniques for capturing and retrieving the circulating tumor cells, such as flow cytometry, cell filtration and immunomagnetic separation, in which the immunomagnetic separation technique is more commonly used. In the process of immunomagnetic separation, a plurality of magnetic beads are added into a sample containing multiple targeted cells. Each of the magnetic beads includes a plurality of antibodies that are able to bind with the targeted cells. After the targeted cells are bound with the antibodies of the magnetic beads, the magnetic beads are collected, achieving separation of the targeted cells from the sample. However, each of the magnetic beads might have multiple targeted cells bound thereon, which results in difficulty in subsequent analyses.

SUMMARY

Therefore, a consideration of the present disclosure is to provide a capturing device, a system and a method for capturing and retrieving biological particles that can alleviate at least one of the drawbacks associated with the prior art.

According to the present disclosure, a biological particle capturing and retrieving system is adapted for retrieving target biological particles from a liquid sample.

The biological particle capturing and retrieving system includes a capturing device and a retrieving device.

The capturing device includes a substrate, an isolating layer and a driving unit. The isolating layer is disposed on the substrate, and includes a top surface, and a plurality of fluidic grooves indented from the top surface and arranged in a herringbone pattern. Each of the fluidic grooves has a bottom surface. The isolating layer further includes a plurality of pores formed in the bottom surface of each of the fluidic grooves. Each of the pores is adapted for capturing a corresponding one of the biological particles. The driving unit includes an electrode array disposed between the substrate and the isolating layer, and a controlling circuit electrically connected to the electrode array. When the controlling circuit applies a voltage to the electrode array, the electrode array drives the liquid sample to flow over the top surface of the isolating layer and through the pores such that the biological particles are captured by the pores. The retrieving device is used for retrieving the biological particles captured in the pores, and includes a micropipette having a tip member and a carrier attached to the tip member and having an outer surface coated with a biological particle-binding material. When the tip member of the micropipette is moved close to one of the pores, the carrier binds with and retrieves the biological particle received in the one of the pores.

According to the present disclosure, a capturing device is adapted for capturing and retrieving target biological particles from a liquid sample. The capturing device includes a substrate, and an isolating layer disposed on the substrate and including a top surface that has a first area, a second area spaced apart from the first area, and a grooved area disposed between the first and second areas. The grooved area has at least one row of first fluidic grooves and at least one row of second fluidic grooves. Each of the rows of the first and second fluidic grooves is arranged in a herringbone pattern extending from the first area to the second area. Each of the first and second fluidic grooves has a bottom surface. The herringbone pattern of the row of the first fluidic grooves points to the second area. The herringbone pattern of the row of the second fluidic grooves points to the first area. The isolating layer further includes a plurality of pores formed in the bottom surface of each of the first and second fluidic grooves and in the top surface outside of the first and second fluidic grooves.

According to the present disclosure, a method is used for capturing and retrieving target biological particles from a liquid sample. The method includes:

providing a capturing device that includes a substrate, an isolating layer disposed on the substrate and including a top surface that has a first area, a second area spaced apart from the first area, and a grooved area disposed between the first and second areas, the grooved area having at least one row of first fluidic grooves and at least one row of second fluidic grooves, each of the rows of the first and second fluidic grooves being arranged in a herringbone pattern extending from the first area to the second area, each of the first and second fluidic grooves having a bottom surface, the herringbone pattern of the row of the first fluidic grooves pointing to the second area, the herringbone pattern of the row of the second fluidic grooves pointing to the first area, the isolating layer further including a plurality of pores formed in the bottom surface of each of the first and second fluidic grooves and in the top surface outside the first and second fluidic grooves;

moving the liquid sample on the top surface of the isolating layer by electrowetting to flow from the first area to the second area through the first fluidic grooves and the pores formed in the first fluidic grooves and thereafter to flow from the second area to the first area through the second fluidic grooves and the pores formed in the second fluidic grooves such that the target biological particles are captured in the pores; and retrieving the target biological particles captured in the pores.

BRIEF DESCRIPTION OF THE DRAWINGS

Other features and advantages of the present disclosure will become apparent in the following detailed description of the embodiment with reference to the accompanying drawings, of which.

DETAILED DESCRIPTION

Figure 1:
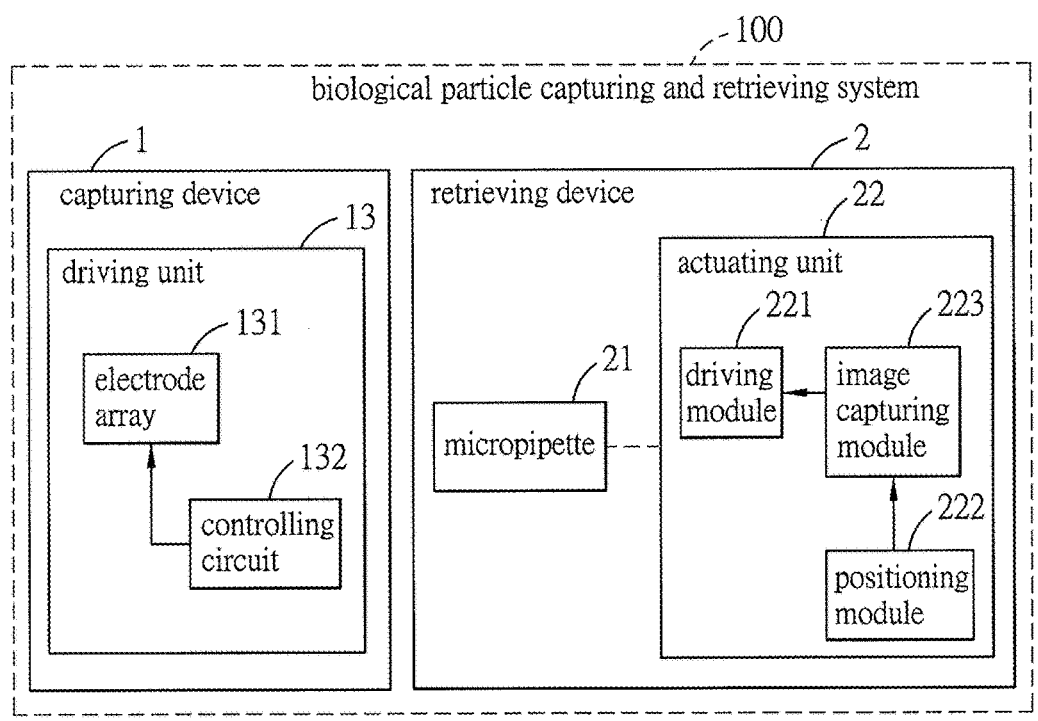
FIG. 1 is a schematic block diagram of an embodiment of the present disclosure, illustrating a biological particle capturing and retrieving system of the embodiment.

Referring to FIG. 1, a biological particle capturing and retrieving system 100 according to an embodiment of the present disclosure is adapted for retrieving target biological particles (not shown) from a liquid sample (not shown). The liquid sample, such as blood, lymph, saliva, urine, etc., may be obtained from an animal subject or a human subject. The target biological particles may be specific biological particles that are of particular interest to an operator of the biological particle capturing and retrieving system 100. For example, the target biological particles may be circulating tumor cells (CTCs), fetal nucleated red blood cells (fNRBCs), trophoblast, viruses, bacteria, etc. Alternatively, the target biological particles may be obtained from plants.

Figure 2:
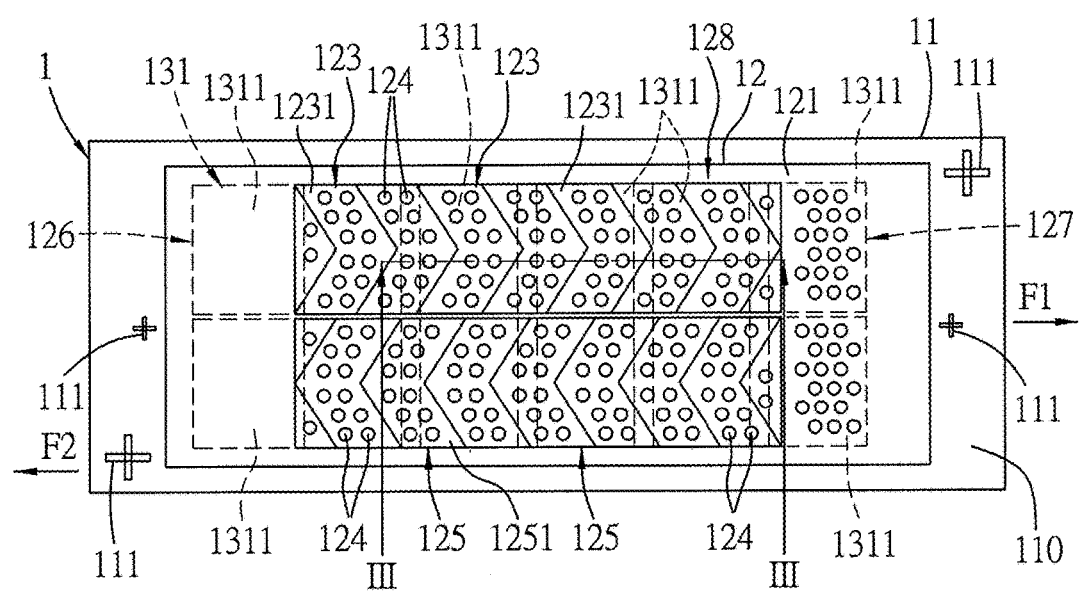
FIG. 2 is a top view of a capturing device of the embodiment.
Figure 3:
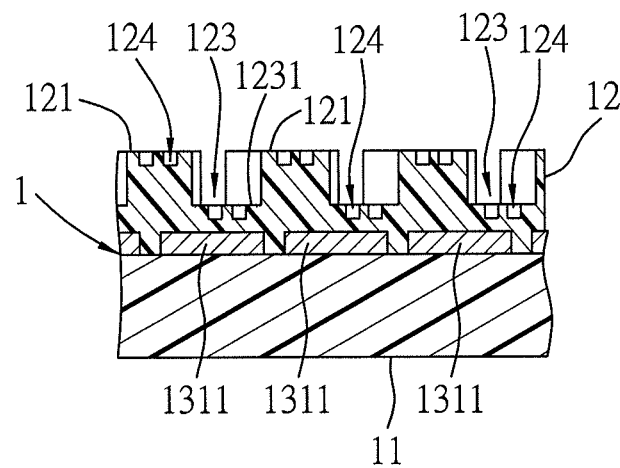
FIG. 3 is a cross sectional view of the capturing device, taken along line III-III of FIG. 2.
Figure 4:
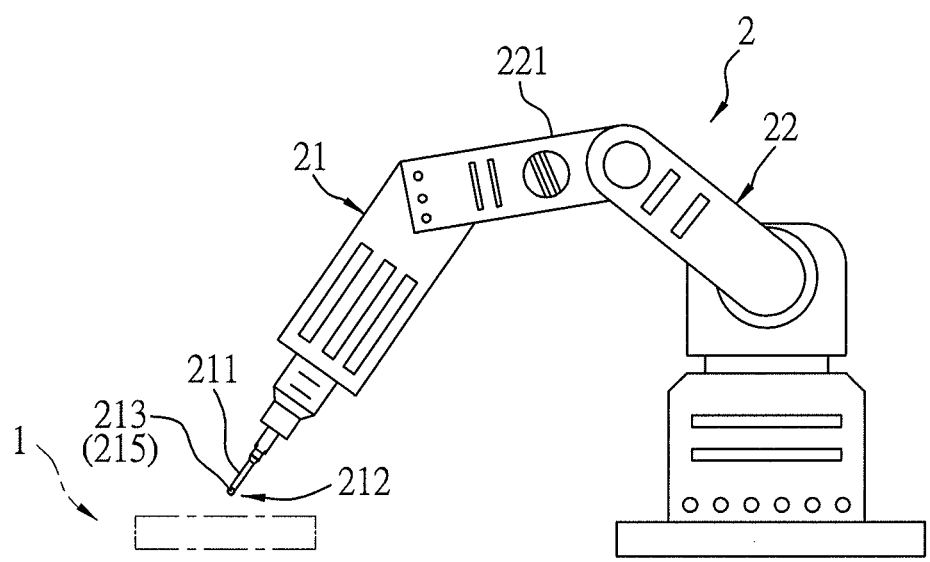
FIG. 4 is a side view of a retrieving device of the embodiment.

Further referring to FIGS. 2, 3 and 4, the biological particle capturing and retrieving system 100 includes a capturing device 1 and a retrieving device 2.

The capturing device 1 includes a substrate 11, an isolating layer 12 and a driving unit 13.

The substrate 11 may be one of a printed circuit board and a glass substrate. Alternatively, the substrate 11 may be made of a material selected from silicon, polymethyl methacrylate and polydimethylsiloxane.

The isolating layer 12 is electrically insulated, is disposed on the substrate 11, and includes a top surface 121, and a plurality of fluidic grooves 123, 125 indented from the top surface 121 and arranged in a herringbone pattern. Specifically, the isolating layer 12 includes the top surface 121 that has a first area 126, a second area 127 spaced apart from the first area 126, and a grooved area 128 disposed between the first and second areas 126, 127. In this embodiment, the fluidic grooves 123, 125 are divided into first fluidic grooves 123 and second fluidic grooves 125, and the grooved area 128 has at least one row of the first fluidic grooves 123 and at least one row of the second fluidic grooves 125. Each of the rows of the first and second fluidic grooves 123, 125 is arranged in a herringbone pattern extending from the first area 126 to the second area 127. The herringbone pattern of the row of the first fluidic grooves 123 points to the second area 127. The herringbone pattern of the row of the second fluidic grooves 125 points to the first area 126. In other words, each of the herringbone patterns of the first fluidic grooves 123 and the second fluidic grooves 125 points in a direction that is the same as a flowing direction (F1, F2) of the liquid sample. Each of the first and second fluidic grooves 123, 125 has a bottom surface 1231, 1251. The isolating layer 12 further includes a plurality of pores 124 formed in the bottom surface 1231, 1251 of each of the first and second fluidic grooves 123, 125 and in the top surface 121 outside of the first and second fluidic grooves 123, 125. Each of the pores 124 is adapted for capturing a corresponding one of the biological particles.

In this embodiment, the top surface 121 are coated with a layer of streptavidin for increasing chemical affinity to the biological particles.

It should be particularly pointed out that, in this embodiment, each of the pores 124 is configured to have a dimension that can accommodate only a single target biological particle. For example, when the target biological particles are circulating tumor cells, each of the pores 124 is configured to have a diameter ranging from 10 μm to 30 μm. On the other hand, when the target biological particles are viruses, each of the pores 124 is configured to have a diameter around 200 nm.

In this embodiment, the substrate 11 has a top surface 110 having an area larger than that of the isolating layer 12 such that a portion of the top surface 110 is not covered by the isolating layer 12. The substrate 11 further has a plurality of position marks 111 that are disposed on the top surface 110 and are spaced apart from and exposed from the isolating layer 12. The position marks 111 are illustrated as four cross marks in FIG. 2, and the number and shape thereof may be changed according to practical requirements.

The driving unit 13 includes an electrode array 131 disposed between the substrate 11 and the isolating layer 12, and a controlling circuit 132 electrically connected to the electrode array 131. In this embodiment, the electrode array 131 includes twelve electrodes 1311 that are arranged in a two-by-six array as shown in FIG. 2. The arrangement of the electrodes 1311 of the electrode array 131 may be changed according to practical requirements. In this embodiment, the controlling circuit 132 is an external circuit connected to the electrode array 131 for applying a voltage to the electrode array 131. Alternatively, the controlling circuit 132 may be integrated into the substrate 11 as an integrated circuit.

When the controlling circuit 132 applies a voltage to the electrode array 131, the electrode array 131 drives the liquid sample to flow by electrowetting (e.g., electrowetting-on-dielectric, EWOD) over the top surface 121 of the isolating layer 12 and through the pores 124 such that the biological particles are captured by the pores 124. By using the electrowetting technique, it is not necessary to use an external pump.

Figure 5:
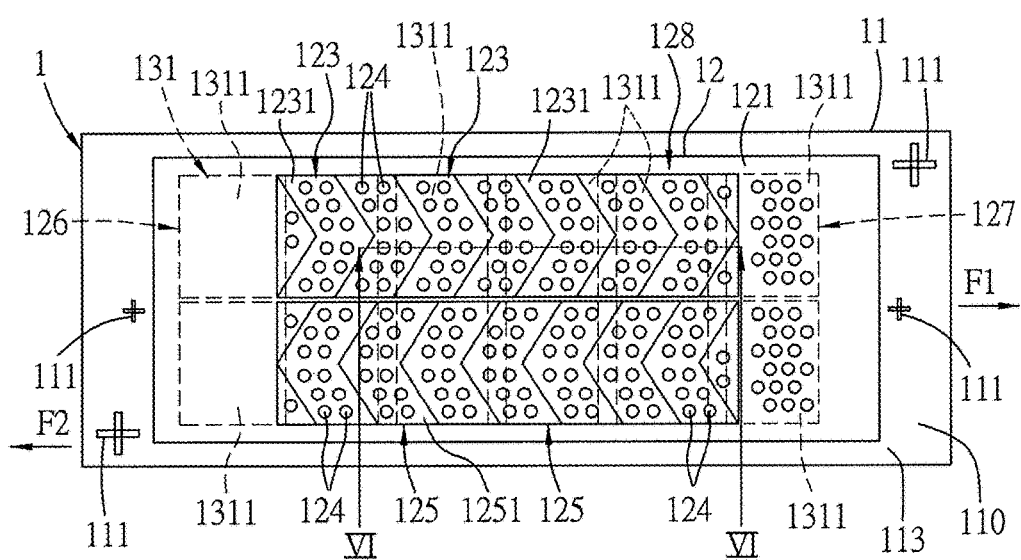
FIG. 5 is a top view of the capturing device, showing an alternative of a substrate of the capturing device.
Figure 6:
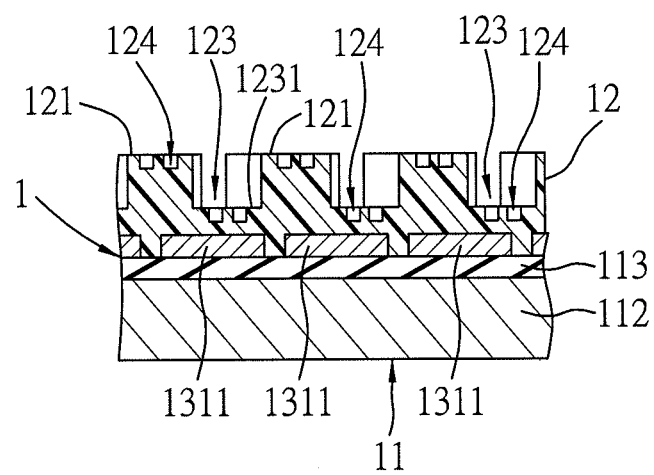
FIG. 6 is a cross sectional view of the capturing device, taken along line VI-VI of FIG. 5 and showing the alternative of the substrate.

Referring to FIGS. 5 and 6, alternatively, the substrate 11 includes a main body 112 that is made of metal (e.g., copper or aluminum), and an insulating film 113 that defines the top surface 110 of the substrate 11 and that is formed between the main body 112 and the electrode array 131 in such a manner that the electrode array 131 is electrically insulated from the main body 112. The insulating film 113 of the substrate 11 may be made of metal oxide (e.g., copper oxide or aluminum oxide). It should be noted that the dimension of the insulating film 113 can be changed based on actual requirements, as long as the electrode array 131 is electrically insulated from the main body 112.

Referring to FIG. 4, the retrieving device 2 is used for retrieving the biological particles captured in the pores 124, and includes a micropipette 21 and an actuating unit 22.

The micropipette 21 has a tip member 211 and a carrier 212 that is attached to the tip member 211 and that has an outer surface 213 coated with a biological particle-binding material, such as epithelial cell adhesion molecule (Ep- CAM) biotinylated antibody. In this embodiment, the carrier 212 includes a magnetic element 215. When the tip member 211 of the micropipette 21 is moved close to one of the pores 124, the carrier 212 binds with and retrieves the biological particle received in the one of the pores 124.

Referring to FIGS. 1 and 4, the actuating unit 22 supports the micropipette 21 and is operable to position the tip member 211 of the micropipette 21 at each of the pores 124 based on the position marks 111.

In this embodiment, the actuating unit 22 includes a driving module 221, an image capturing module 222 and a positioning module 223. The driving module 221 is used for driving movement of the micropipette 21. The image capturing module 222 is used for capturing images of the top surface 121 of the isolating layer 12 and the position marks 111. The positioning module 223 is electrically coupled to the driving module 221 and the image capturing module 222, receives the image captured by the image capturing module 222, and controls the driving module 221 based on the image.

According to the embodiment of this disclosure, a method for capturing and retrieving the target biological particles from the liquid sample includes:

providing the aforesaid capturing device 1 as shown in FIG. 2;

moving the liquid sample on the top surface 121 of the isolating layer 12 by electrowetting to flow from the first area 126 to the second area 127 in the flowing direction (F1) through the first fluidic grooves 123 and the pores 124 formed in the first fluidic grooves 123 and thereafter to flow from the second area 127 to the first area 126 in the flowing direction (F2) through the second fluidic grooves 125 and the pores 124 formed in the second fluidic grooves 125 such that the target biological particles are captured in the pores 124; and retrieving the target biological particles captured in the pores 124 using the retrieving device 2.

The step of moving the liquid sample is performed by the driving unit 13.

In this embodiment, the steps of retrieving the target biological particles includes:

moving the tip member 211 of the micropipette 21 close to one of the pores 124 that captures a corresponding one of the target biological particles; and retrieving the corresponding target biological particle from the one of the pores 124 through use of the carrier 212 that is attached to the tip member 211 and that is coated with the biological particle-binding material capable of binding with and isolating the target biological particle(s) from each of the pores 124.

The method may further include, before the retrieving step:

labeling the target biological particles captured in the pores 124 with fluorescent staining; and positioning the tip member 211 with respect to the target biological particles with fluorescent staining by locating each of the pores 124 that captures the target biological particles with reference to the position marks 111.

It is worth mentioning that the use of electrowetting-on-dielectric structure and herringbone pattern in the step of moving the liquid sample decreases laminar flow and precipitation of the liquid sample.

In this embodiment, the fluorescent staining technique is an immunofluorescence technique and may be changed according to practical requirements. The image capturing module 222 captures the image of the target biological particles with fluorescent staining. The positioning module 223 receives the captured image from the image capturing module 222 and locates each of the pores 124 with reference to the position marks 111 based on the image captured by the image capturing module 222. The driving module 221 is controlled by the positioning module 223 based on the locating information thus obtained to position the tip member 211.

It is worth mentioning that the target biological particle attached to the carrier 212 may be detached from the carrier 212 by means of physical or chemical techniques. For example, the carrier 212 along with the attached target biological particle can be immersed into Trypsin to detach the target biological particle from the carrier 212 to obtain a single target biological particle for subsequent analysis or any other applications.

With the first and second fluidic grooves 123, 125, and the pores 124, each of the target biological particles can be captured in a corresponding one of the pores 124. In addition, the use of the electrowetting-on-dielectric technique decreases laminar flow and precipitation of the liquid sample. The biological particle-binding material coated on the outer surface 213 of the carrier 212 enables the retrieving of a single target biological particle from the corresponding pore 124.

In the description above, for the purposes of explanation, numerous specific details have been set forth in order to provide a thorough understanding of the embodiment. It will be apparent, however, to one skilled in the art, that one or more other embodiments may be practiced without some of these specific details. It should also be appreciated that reference throughout this specification to "one embodiment," "an embodiment," an embodiment with an indication of an ordinal number and so forth means that a particular feature, structure, or characteristic may be included in the practice of the disclosure. It should be further appreciated that in the description, various features are sometimes grouped together in a single embodiment, figure, or description thereof for the purpose of streamlining the disclosure and aiding in the understanding of various inventive aspects.

While the disclosure has been described in connection with what is considered the exemplary embodiment, it is understood that this disclosure is not limited to the disclosed embodiment but is intended to cover various arrangements included within the spirit and scope of the broadest interpretation so as to encompass all such modifications and equivalent arrangements.

What is claimed is:

1. A biological particle capturing and retrieving system adapted for retrieving target biological particles from a liquid sample, said biological particle capturing and retrieving system comprising:
   a capturing device including
      a substrate,
      an isolating layer disposed on said substrate, and including a top surface, and a plurality of fluidic grooves indented from said top surface and arranged in a herringbone pattern, each of said fluidic grooves having a bottom surface, said isolating layer further including a plurality of pores formed in said bottom surface of each of said fluidic grooves, each of said pores being adapted for capturing a corresponding one of the biological particles, and
      a driving unit that includes an electrode array disposed between said substrate and said isolating layer, and a controlling circuit electrically connected to said electrode array, wherein when said controlling circuit applies a voltage to said electrode array, said electrode array driving the liquid sample to flow over said top surface of said isolating layer and through said pores such that the biological particles are captured by said pores; and a retrieving device for retrieving the biological particles captured in said pores, said retrieving device including a micropipette having a tip member and a carrier attached to said tip member and having an outer surface coated with a biological particle-binding material, wherein when said tip member of said micropipette is moved close to one of said pores, said carrier binds with and retrieves the biological particle received in said one of said pores.

2. The biological particle capturing and retrieving system as claimed in claim 1, wherein said herringbone pattern of said fluidic grooves points in a direction that is the same as a flowing direction of the liquid sample.

3. The biological particle capturing and retrieving system as claimed in claim 1, wherein said electrode array drives the liquid sample by electrowetting technique.

4. The biological particle capturing and retrieving system as claimed in claim 1, wherein said carrier includes a magnetic element.

5. The biological particle capturing and retrieving system as claimed in claim 1, wherein:

said substrate has a plurality of exposed position marks spaced apart from said isolating layer; and said retrieving device further includes an actuating unit that supports said micropipette and that is operable to position said tip member of said micropipette at each of said pores based on said position marks.

6. The biological particle capturing and retrieving system as claimed in claim 1, wherein said substrate is one of a printed circuit board and a glass substrate.

7. The biological particle capturing and retrieving system as claimed in claim 1, wherein said substrate is made of a material selected from the group consisting of silicon, polymethyl methacrylate and polydimethylsiloxane.

8. The biological particle capturing and retrieving system as claimed in claim 1, wherein said substrate includes a main body that is made of metal, and an insulating film that is formed between said main body and said electrode array of said driving unit in such a manner that said electrode array is electrically insulated from said main body.

9. The biological particle capturing and retrieving system as claimed in claim 8, wherein said insulating film of said substrate is made of metal oxide.

\* \* \* \* \*